United States Patent [19]

Tilly et al.

[11] 4,107,286
[45] Aug. 15, 1978

[54] POLYIODS BENZENE DERIVATIVES AND X-RAY CONTRAST MEDIA CONTAINING THE SAME

[75] Inventors: Guy Tilly; Michel Jean-Charles Hardouin; Jean Lautrou, all of Aulnay-sous-Bois, France

[73] Assignee: Guerbet S.A., Aulnay-sous-Bois, France

[21] Appl. No.: 782,413

[22] Filed: Mar. 29, 1977

[30] Foreign Application Priority Data

Apr. 8, 1976 [GB] United Kingdom ............... 14343/76

[51] Int. Cl.$^2$ ..................... A61K 29/02; C07C 101/42
[52] U.S. Cl. .................................. 424/5; 260/501.11; 260/518 A; 560/42; 560/47
[58] Field of Search .............. 260/501.11, 518 A; 424/5; 560/42, 47

[56] References Cited

U.S. PATENT DOCUMENTS

| | | | |
|---|---|---|---|
| 3,886,203 | 5/1975 | Felder et al. | 260/501.11 |
| 3,910,989 | 10/1975 | Felder et al. | 424/5 |
| 4,001,298 | 1/1977 | Gries et al. | 560/47 |
| 4,014,986 | 3/1977 | Tilly et al. | 560/47 |

Primary Examiner—James O. Thomas, Jr.
Assistant Examiner—G. T. Breitenstein
Attorney, Agent, or Firm—Young & Thompson

[57] ABSTRACT

This invention relates to compounds of the formula:

$$\text{A—NH—CO} \begin{array}{c} R_1 \\ | \\ N-COR_2 \\ \end{array} \text{CO—NH—A} \qquad (I)$$

(with I substituents on the benzene ring)

in which:
$R_1$ represents a hydrogen atom or a $C_{1-4}$ alkyl radical or a $C_{1-4}$ hydroxyalkyl radical,
$R_2$ represents a $C_{1-4}$ alkyl radical or a $C_{1-4}$ hydroxyalkyl radical,
A represents a group of the formula:

$$\begin{array}{c} \text{COOH} \\ | \\ \text{I} \quad \text{I} \\ R_3 \quad (CH_2)_a - N - CO(CH_2)_n \\ | \quad \quad | \\ \text{I} \quad R_4 \end{array}$$

in which:
$R_3$ represents a hydrogen atom, a group of the formula $$-CON\begin{array}{c} R_5 \\ \diagdown \\ R_6 \end{array}$$

in which $R_5$ and $R_6$ represent each a hydrogen atom or a $C_{1-4}$ alkyl radical or a $C_{1-4}$ hydroxyalkyl radical, or a group of the formula $$\begin{array}{c} -N-COR_7 \\ | \\ R_8 \end{array}$$

in which $R_7$ represents a $C_{1-4}$ alkyl radical or a $C_{1-4}$ hydroxyalkyl radical and $R_8$ represents a hydrogen atom, a $C_{1-4}$ alkyl radical or a $C_{1-4}$ hydroxyalkyl radical,
$a$ is 0 or 1 and $n$ is an integer from 1 to 5 inclusive,
$R_4$ represents a hydrogen atom or a $C_{1-4}$ alkyl radical or a $C_{1-4}$ hydroxyalkyl radical, their methyl and ethyl esters and their salts with pharmaceutically acceptable bases.

Said compounds are useful as X-ray contrast media.

8 Claims, No Drawings

POLYIODS BENZENE DERIVATIVES AND X-RAY CONTRAST MEDIA CONTAINING THE SAME

This invention relates to new polyiodo benzene derivatives useful as X-ray contrast media.

More particularly, the present invention relates to new compounds having three triiodo benzene nuclei.

The present invention relates to compounds of the formula:

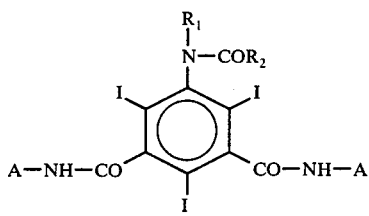

in which:

$R_1$ represents a hydrogen atom or a $C_{1-4}$ alkyl radical or a $C_{1-4}$ hydroxyalkyl radical, $R_2$ represents a $C_{1-4}$ alkyl radical or a $C_{1-4}$ hydroxyalkyl radical, A represents a group of the formula:

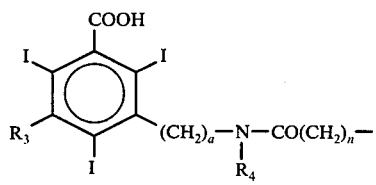

in which:

$R_3$ represents a hydrogen atom, a group of the formula

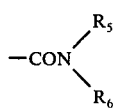

in which $R_5$ and $R_6$ represent each a hydrogen atom or a $C_{1-4}$ alkyl radical or a $C_{1-4}$ hydroxyalkyl radical, or a group of the formula

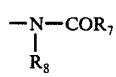

in which $R_7$ represents a $C_{1-4}$ alkyl radical or a $C_{1-4}$ hydroxyalkyl radical and $R_8$ represents a hydrogen atom, a $C_{1-4}$ alkyl radical or a $C_{1-4}$ hydroxyalkyl radical, $a$ is 0 or 1 and $n$ is an integer from 1 to 5 inclusive, $R_4$ represents a hydrogen atom or a $C_{1-4}$ alkyl radical or a $C_{1-4}$ hydroxyalkyl radical, their methyl and ethyl esters and their salts with pharmaceutically acceptable bases.

An advantageous class of the compounds of the formula (I) is that in which:

$R_1$ represents a hydrogen atom, $R_2$ represents a $C_{1-4}$ alkyl radical,

A represents a group of the formula:

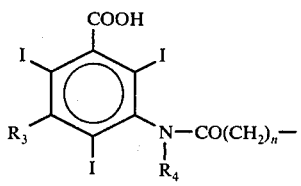

in which:

$R_3$ represents a hydrogen atom, a group of the formula $-CO-NR_5R_6$ in which $R_5$ is a hydrogen atom and $R_6$ is a $C_{1-4}$ alkyl radical or a $C_{1-4}$ hydroxyalkyl radical, or a group of the formula $-NR_8COR_7$ in which $R_7$ is a $C_{1-4}$ alkyl radical and $R_8$ is a hydrogen atom or a $C_{1-4}$ alkyl radical, $n$ is an integer from 1 to 5 inclusive, and $R_4$ represents a hydrogen atom or a $C_{1-4}$ alkyl radical; and their ethyl or methyl esters and their salts with pharmaceutically acceptable bases.

Salts of acids of the formula (I) include typically alkali metal salts (e.g., sodium and potassium salts), ammonium salts, alkaline-earth metal salts (e.g., calcium salts) and salts with organic bases such as ethanolamine, cyclohexylamine or methylglucamine.

The compounds of the formula (I) may be prepared by reacting an acid dichloride of the formula:

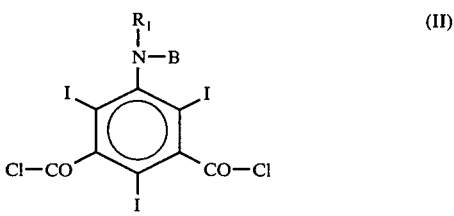

in which $R_1$ has the above-defined meaning and B represents a hydrogen atom or a radical $-COR_2$ in which $R_2$ has the above-defined meaning, with an amine of the formula $A-NH_2$ in which A has the above-defined meaning and, in the case where B is a hydrogen atom, reacting the resulting compound with an acid chloride of the formula $Cl-COR_2$ or an anhydride of the formula $(R_2CO)_2O$, in which $R_2$ has the above-defined meaning, and optionally saponifying the ester functions resulting from the action of acid chloride $ClCOR_2$ on the hydroxy groups, if present.

Thus, the process includes two embodiments which both use the same starting materials: which embodiments comprise either first preparing from a dichloride of the formula (II) in which B = H a compound of the formula (II) in which B = $COR_2$ by acylation of the group >NH with $ClCOR_2$ and then reacting the acylated dichloride with an amine $ANH_2$; or reacting the dichloride of the formula (II) in which B = H with an amine $ANH_2$ and then acylating with $ClCOR_2$ the >NH group of the resulting compound, and then saponifying the ester group which may have formed because of the presence of any hydroxy groups in the various substituents.

The acylation reaction or reactions of $A-NH_2$ with the dichloride of the formula (II) may be effected under the usual conditions for condensing acid chlorides with amines, for example within a polar solvent such as DMAC, or DMSO or dioxane, at a temperature of about 15° C to about 100° C, in the presence of an acid binding agent.

Said reaction or reactions may be followed by a N-alkylation or a N-hydroxyalkylation reaction or by a salt-forming reaction under the conventional conditions for said reactions.

The following non limiting Examples illustrate the present invention.

EXAMPLE 1

Preparation of
2,4,6-triiodo-5-acetamido-1,3-bis-[2,4,6-triiodo-3-N-hydroxyethyl carbamoyl-5-carboxy-phenyl)carbamoyl methyl carbamoyl]benzene

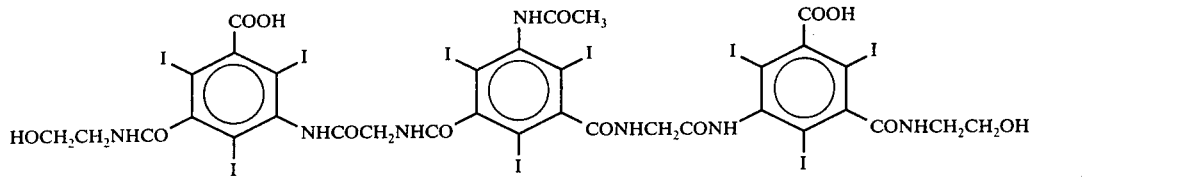

(a) Preparation of 2,4,6-triiodo-5-acetamido-isophthalic acid dichloride

To 2,4,6-triiodo-5-amino-isophthalic acid dichloride (150 g; 0.252 mole) in DMAC (300 ml) is added acetyl chloride (80 ml; 4 times the theoretical amount). The mixture is stirred overnight in an ice-water bath. It is then poured over water (1.5 liter). The resulting material is then filtered and washed twice with water, after which it is dried in an oven at 45° C, to give 159 g of product (i.e., in a yield of 99%).

Purity is controlled by:
Thin layer chromatography over silicagel plate; eluent:benzene/methyl ethyl ketone/formic acid (60:25:20).

Unacetylated product: Rf = 0.90
Acetylated product: Rf = 0.85
Iodine titration: 99%
Chlorine titration: 99%

(b) The acid dichloride (158 g; 0.249 mole) obtained in (a) is poured over a mixture of 2,4,6-triiodo-3-N-hydroxyethyl-carbamoyl-5-aminoacetamido-benzoic acid (328 g; 0.498 mole), DMAC (650 ml) and triethylamine (140 ml) which is then stirred overnight at 50° C. The reaction mixture is then poured over water (3.3 liters) and precipitated with pure HCl. After filtration, the material is washed with water and redissolved in 2N NaOH. The pH is adjusted to a value of 6-7 with acetic acid and the material is charcoaled overnight at 60° C. The charcoal is then filtered off, after which the resulting material is precipitated with pure HCl. After filtration and washing twice with water, the precipitate is dried in an oven, to give 103 g of product (i.e., in a yield of 22%).

(c) Purification via the sodium salt

To the product obtained in (b) (55 g) is added water (165 ml) and 17N NaOH to adjust the pH to a value of 7-8. The material is then heated at 85° C and 17N NaOH (275 g) is added thereto. After cooling to room temperature, the reaction mixture is allowed to crystallize overnight in the refrigerator, crystallization being initiated by scratching the walls of the container. After filtration, the product is made clear with 10N NaOH, after which it is dissolved in water (150 ml) and precipitated with pure HCl.

After filtration and washing once with water, the resulting material is dried in an oven, to give 20 g of cream-coloured product.

Purity is controlled by:
Thin layer chromatography over silicagel plate. Eluent: ethyl acetate/isopropanol/ammonia (25:35:40).
Starting amine: Rf = 0.40
Acid dichloride: Rf = 1.00
Product: Rf = 0.30
Iodine titration: 101%
Titration with sodium methoxide: 100%

EXAMPLE 2

Preparation of
2,4,6-triiodo-5-acetamido-1,3-bis-[2,4,6-triiodo-3-methylcarbamoyl-5-carboxy-phenyl)carbamoyl-methylcarbamoyl]benzene

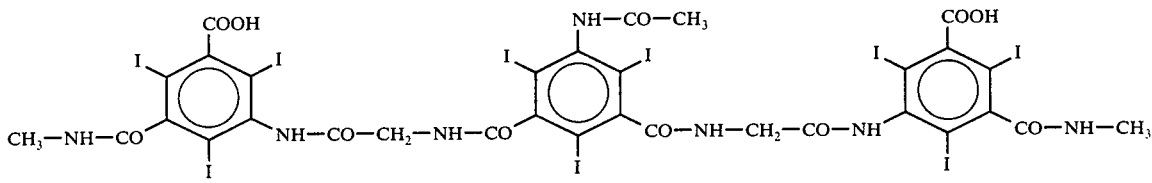

The compound is prepared by condensation of the acid chloride obtained in Example 1(a) with 2,4,6-triiodo-3-methylcarbamoyl-5-aminoacetamido-benzoic acid in DMAC, according to the procedure described in Example 1.

Purity is controlled by:
Thin layer chromatography over silicagel plate. Eluent: ethyl acetate/isopropanol/ammonia (25:35:40)
Starting amine: Rf = 0.6
Product: Rf = 0.55
Butanol/water/acetic acid (50:25:13)
Starting amine: Rf = 0.2
Product: Rf = 0.15
Iodine titration: 100.2%
Titration with sodium methoxide: 99%

EXAMPLE 3

Preparation of 2,4,6-triiodo-5-acetamido-1,3-bis-[2,4,6-triiodo-5-carboxy-phenyl)-carbamoyl-methyl-carbamoyl]benzene

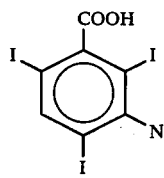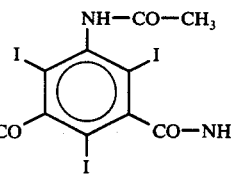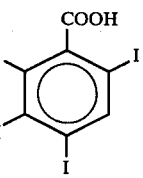

The compound is prepared by condensation of the acid chloride obtained in Example 1(a) with 2,4,6-triiodo-3-amino-acetamido-benzoic acid in DMAC, according to the procedure described in Example 1.

Purity is controlled by:

Thin layer chromatography over silicagel plate. Eluent: butanol/water/acetic acid (50:25:13)

Starting amine: Rf = 0.20
Product: Rf 32 0.15
Iodine titration: 99.2%
Titration with sodium methoxide: 99%

EXAMPLE 5

Preparation of 2,4,6-triiodo-5-acetamido-1,3-bis-[(2,4,6-triiodo-3-N-methyl-acetamido-5-carboxy-phenyl)-carbamoyl-methyl-carbamoyl]benzene

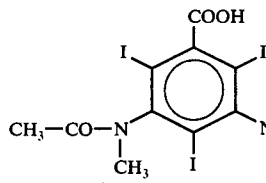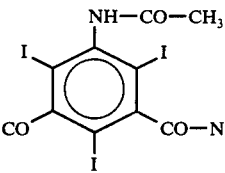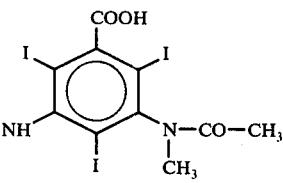

Starting amine: Rf = 0.37
Product: Rf = 0.43
benzene/methylethylketone/formic acid (60:25:10)
Starting amine: Rf = 0.00
Product: Rf = 0.15
Iodine titration: 101%
Titration with sodium methoxide: 100.2%

The compound is prepared by condensation of the acid chloride obtained in Example 1(a) with 2,4,6-triiodo-3-N-methylacetamido-5-aminoacetamido-benzoic acid in DMAC, according to the procedure described in Example 1.

Purity is controlled by:
Thin layer chromatography over silicagel plate.
Eluent: butanol/water/acetic acid (50:25:13)
Starting amine: Rf = 0.20
Product: Rf = 0.25
Iodine titration: 98.6%
Titration with sodium methoxide: 99.3%

EXAMPLE 4

Preparation of 2,4,6-triiodo-5-acetamido-1,3-bis[(2,4,6-triiodo-3-acetamido-5-carboxy-phenyl)carbamoyl-methyl-carbamoyl]benzene

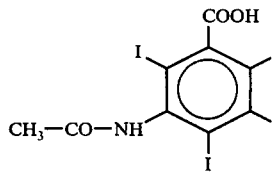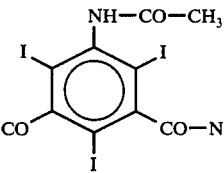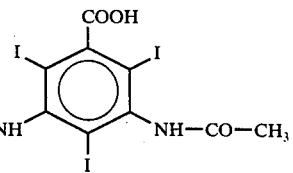

The compound is prepared by condensation of the acid chloride obtained in Example 1(a) with 2,4,6-triiodo-3-acetamido-5-aminoacetamido-benzoic acid in DMAC, according to the procedure described in Example 1.

Purity is controlled by:

EXAMPLE 6

Preparation of 2,4,6-triiodo-5-acetamido-1,3-bis-[(2,4,6-triiodo-3-N-hydroxyethylcarbamoyl-5-carboxy-phenyl)-N-methyl-carbamoyl-methyl-carbamoyl]benzene

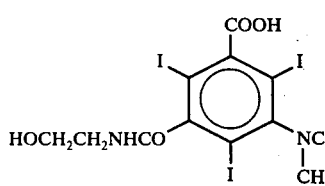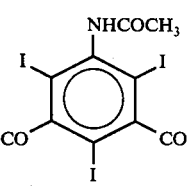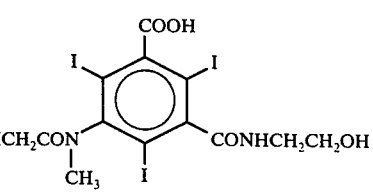

The compound is prepared by condensation of the acid chloride obtained in Example 1(a) with 2,4,6-triiodo-3-N-hydroxyethylcarbamoyl-5-amino-N-methyl acetamido-benzoic acid in DMAC, according to the procedure described in Example 1.

Purity is controlled by thin layer chromatography on silicagel plate. Eluent: butanol/water/acetic acid (50:25:13)

Starting amine: Rf = 0.23
Product: Rf = 0.17

In the following Table are given results which demonstrate the low toxicity of the compounds of this invention, as compared with currently used contrast media.

| Compounds | I.V. Toxicity in mice, 2 ml/mn | Osmolality (mosm/kg) solution containing 28% iodine |
|---|---|---|
| Example 1 (Na salt) | Solution containing 35% iodine 11 g/kg | 650 |
| (a) (methylglucamine salt) | Solution containing 28% iodine 5.4 g/kg | 1410 |
| (b) Solution containing (methylglucamine salt) | 30% iodine 5.6 g/kg | 1390 |
| (c) (methylglucamine salt) | Solution containing 28% iodine 6.7 g/kg | 950 |
| (d) (mixed Mgl and Na salts) | Solution containing 38% iodine 5.7 g/kg | |

(a), (b), (c) and (d) are the following reference materials:
a - 2,4,6-triiodo-3-methylcarbamoyl-5-acetamido-benzoic acid (iothalamic acid)
b - 2,4,6-triiodo-3-N-hydroxyethylcarbamoyl-5-acetamido-benzoic acid (ioxithalamic acid)
c - 5,5'-(adipoly-diimino)-bis-(2,4,6-triiodo-N-methyl)-isophthalamic acid (iocarmic acid)
d - 2,4,6-triiodo-3,5-bis(acetamido)benzoic acid (diatrizoic acid).

The compounds of the present invention are useful as X-ray contrast media.

The preferred pharmaceutical form consists of aqueous solutions of salts of the compounds of the formula (I).

The aqueous solutions contain advantageously from 5 g to 100 g of salt of a compound of the formula (I) per 100 ml, and the injectable amount of such solutions may vary from 5 ml to 1000 ml.

Having now described our invention what we claim as new and desire to secure by Letters Patent is:

1. A compound selected from a compound of the formula:

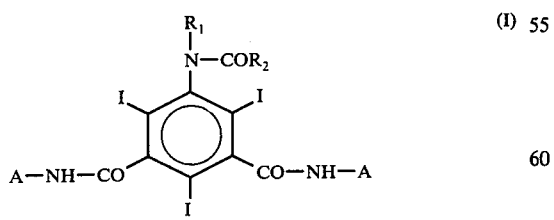

in which:
$R_1$ is selected from hydrogen, $C_{1-4}$ alkyl and $C_{1-4}$ hydroxyalkyl,
$R_2$ is selected from $C_{1-4}$ alkyl and $C_{1-4}$ hydroxyalkyl,
A represents a group of the formula:

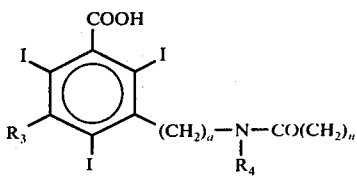

in which:
$R_3$ is selected from: hydrogen; a group of the formula

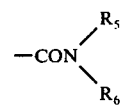

in which $R_5$ and $R_6$ are independently selected from hydrogen, $C_{1-4}$ alkyl and $C_{1-4}$ hydroxyalkyl; and a group of the formula

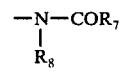

in which $R_7$ is selected from $C_{1-4}$ alkyl and $C_{1-4}$ hydroxyalkyl and $R_8$ is selected from hydrogen, $C_{1-4}$ alkyl and $C_{1-4}$ hydroxyalkyl,
$a$ is an integer from 0 to 1 and $n$ is an integer from 1 to 5,
$R_4$ is selected from hydrogen, $C_{1-4}$ alkyl and $C_{1-4}$ hydroxyalkyl, its methyl and ethyl esters and its salt with a pharmaceutically acceptable base.

2. A compound as defined in claim 1, in which:
$R_1$ is hydrogen,
$R_2$ is $C_{1-4}$ alkyl,
A represents a group of the formula:

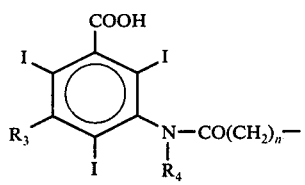

in which:
$R_3$ is selected from: hydrogen; a group of the formula —CO—$NR_5R_6$ in which $R_5$ is hydrogen and $R_6$ is selected from $C_{1-4}$ alkyl and $C_{1-4}$ hydroxyalkyl; and a group of the formula —$NR_8COR_7$ in which $R_7$ is $C_{1-4}$ alkyl and $R_8$ is selected from hydrogen and $C_{1-4}$ alkyl,
$n$ is an integer from 1 to 5 inclusive, and
$R_4$ is selected from hydrogen and $C_{1-4}$ alkyl.

3. 2,4,6-Triiodo-5-acetamideo-1,3-bis[(2,4,6-triiodo-3-N-hydroxyethylcarbamoyl-5-carboxy-phenyl)-carbamoyl-methyl-carbamoyl]benzene or a salt thereof with a pharmaceutically acceptable base.

4. X-ray contrast medium, comprising an effective amount of a compound selected from a compound of the formula:

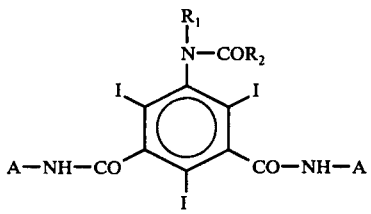

in which:

$R_1$ is selected from hydrogen, $C_{1-4}$ alkyl and $C_{1-4}$ hydroxyalkyl, $R_2$ is selected from $C_{1-4}$ alkyl and $C_{1-4}$ hydroxyalkyl, A represents a group of the formula:

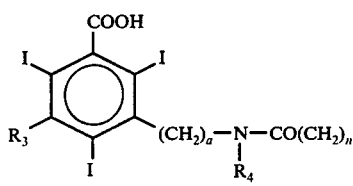

in which:

$R_3$ is selected from: hydrogen; a group of the formula

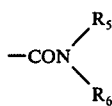

in which $R_5$ and $R_6$ are independently selected from hydrogen, $C_{1-4}$ alkyl and $C_{1-4}$ hydroxyalkyl; and a group of the formula

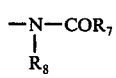

in which $R_7$ is selected from $C_{1-4}$ alkyl, and $C_{1-4}$ hydroxyalkyl and $R_8$ is selected from hydrogen, $C_{1-4}$ and $C_{1-4}$ hydroxyalkyl, $a$ is an integer from 0 to 1 and $n$ is an integer from 1 to 5, $R_4$ is selected from hydrogen, $C_{1-4}$ alkyl and $C_{1-4}$ hydroxyalkyl, its methyl and ethyl esters and its salt with a pharmaceutically acceptable base, in a pharmaceutically acceptable carrier.

5. X-ray contrast medium as claimed in claim 4, wherein in said compound of the formula (I):

$R_1$ is hydrogen, $R_2$ is $C_{1-4}$ alkyl,

A represents a group of the formula:

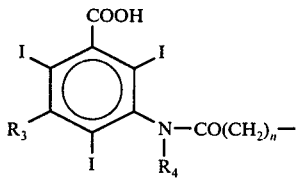

in which:

$R_3$ is selected from: hydrogen; a group of the formula $-CO-NR_5R_6$ in which $R_5$ is hydrogen and $R_6$ is selected from $C_{1-4}$ alkyl and $C_{1-4}$ hydroxyalkyl; and a group of the formula $-NR_8COR_7$ in which $R_7$ is $C_{1-4}$ alkyl and $R_8$ is selected from hydrogen and $C_{1-4}$ alkyl, $n$ is an integer from 1 to 5 inclusive, and $R_4$ is selected from hydrogen and $C_{1-4}$ alkyl.

6. X-ray contrast medium as claimed in claim 5, wherein said compound is 2,4,6-triiodo-5-acetamido-1,3-bis[(2,4,6-triiodo-3-N-hydroxyethyl carbamoyl-5-carboxyphenyl)carbamoyl-methyl-carbamoyl]benzene or a salt thereof with a pharmaceutically acceptable base.

7. X-ray contrast medium as claimed in claim 4, formulated as an aqueous solution of a pharmaceutically acceptable salt of a compound of the formula (I).

8. X-ray contrast medium as claimed in claim 7, wherein said aqueous solution comprises 5–100 g of salt of a compound of the formula (I) per 100 ml of solution.

* * * * *